US008349802B2

(12) United States Patent
Gulati et al.

(10) Patent No.: US 8,349,802 B2
(45) Date of Patent: *Jan. 8, 2013

(54) METHODS AND COMPOSITIONS FOR CONTRIBUTING TO THE TREATMENT OF CANCERS

(75) Inventors: Anil Gulati, Naperville, IL (US); Guru Reddy, Irvine, CA (US); Luigi Lenaz, Newtown, PA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/220,373

(22) Filed: Aug. 29, 2011

(65) Prior Publication Data

US 2011/0311481 A1 Dec. 22, 2011

Related U.S. Application Data

(63) Continuation of application No. 12/101,008, filed on Apr. 10, 2008, now Pat. No. 8,026,216, and a continuation-in-part of application No. 11/461,961, filed on Aug. 2, 2006, now abandoned, which is a continuation-in-part of application No. 11/360,236, filed on Feb. 22, 2006, and a continuation-in-part of application No. 10/691,915, filed on Oct. 23, 2003, now abandoned.

(60) Provisional application No. 60/911,773, filed on Apr. 13, 2007, provisional application No. 60/655,656, filed on Feb. 22, 2005, provisional application No. 60/655,654, filed on Feb. 22, 2005, provisional application No. 60/655,643, filed on Feb. 22, 2005, provisional application No. 60/420,960, filed on Oct. 24, 2002.

(51) Int. Cl.
*A61K 38/10* (2006.01)
*A61K 38/20* (2006.01)
*A61K 38/21* (2006.01)

(52) U.S. Cl. ............ 514/16.1; 514/19.3; 514/21.5; 424/85.2; 424/85.4; 424/85.5; 424/85.6; 424/85.7

(58) Field of Classification Search .................. None
See application file for complete search history.

(56) References Cited

U.S. PATENT DOCUMENTS

| 5,550,110 | A | 8/1996 | Cody et al. |
| 5,612,359 | A | 3/1997 | Murugesan |
| 5,811,416 | A | 9/1998 | Chwalisz et al. |
| 7,976,835 | B2 | 7/2011 | Gulati |
| 2002/0082285 | A1 | 6/2002 | Lebwohl |
| 2003/0104976 | A1* | 6/2003 | Davar et al. ............ 514/1 |
| 2004/0138121 | A1 | 7/2004 | Gulati |
| 2006/0211617 | A1 | 9/2006 | Gulati |
| 2007/0032422 | A1 | 2/2007 | Gulati |
| 2008/0253994 | A1 | 10/2008 | Gulati |
| 2008/0318846 | A1 | 12/2008 | Gulati |
| 2009/0155206 | A1 | 6/2009 | Gulati |

FOREIGN PATENT DOCUMENTS

| EP | 0655463 A1 | 5/1995 |
| EP | 0815870 A2 | 1/1998 |
| EP | 0950418 A2 | 10/1999 |
| WO | 96/19233 | 6/1996 |
| WO | 00/67024 | 11/2000 |
| WO | 01/00198 | 1/2001 |
| WO | 01/00198 A2 | 1/2001 |
| WO | 01/91736 | 12/2001 |
| WO | 03/009805 | 2/2003 |
| WO | 03/045434 | 6/2003 |
| WO | 2004/037235 | 5/2004 |
| WO | 2006/091767 | 8/2006 |

OTHER PUBLICATIONS

Battistini et al. "Endothelins: A Quantum Leap Forward", Drug News & Perspectives, Aug. 1995, pp. 365-391, vol. 8, No. 6.
Bell et al., "A Comparative Study of Tumor Blood Flow Modification in two Rat Tumor Systems Using Endothelin-1 and Angiotensin II: Influence of Tumor Size on Angiotensin II Response", copyright 1996, pp. 730-738, vol. 67, No. 5.
Bell et al., "Vascular Response of Tumor and Normal Tissues to Endothelin-1 following Antagonism of ETa and ETb Receptors in Anaesthetised Rats", Int. J. Cancer, copyright 1997, pp. 283-289, vol. 73, No. 2Int. J. Cancer.
Bell et al., Modification of Blood Flow in the HSN Tumor and Normal Tissues of the Rat by the Endothelin ETb Receptor Agonist, IRL 1620, Int. J. Cancer, copyright 1999, pp. 295-302, vol. 80, No. 2.
Bell et al. "Effect of Endothelin-1 and Sarafotoxin S6c on Blood Flow in a Rat Tumor", Journal of Cardiovascular Pharmacology, copyright 1995, pp. S222-225, vol. 26 (Suppl.3).
Bell et al. "Tumor blood flow modification by endothelin-related peptides in the rat HSN fibrosarcoma", British Journal of Cancer, copyright 1996, pp. S161-S163, Supp.27.
Bhalia et al., "Potentiation of morphine analgesia by BQ123, an endothelin antagonist", Peptides, copyright 2002, pp. 1837-1845 vol. 23.
Bhargave et al., Modification of Brain and Spinal Cord Dopamine D1 Receptors Labeled with [3H]SCH 23390 After Morphine Withdrawal from Tolerant and Physically Dependent Rats, The Journal of Pharmacology and Experimental Therapeutics, copyright 1990, pp. 901-907 vol.252, No. 3.
Chaplin et al., "Modification of Tumor Blood Flow: Current Status and Future Directions", Seminars in Radiation Oncology, Jul. 1998, pp. 151-163, vol. 8, No. 3.
Davar et al., "Behavioral signs of acute pain produced by application of endothelin-1 to rat sciatic nerve", NeuroReport, copyright 1998, pp. 2279-2283, vol. 9, No. 10.
Davenport, International Union of Pharmacology. XXIX. Update on Endothelin Receptor Nomenclature, Journal, Pharmacological Reviews, vol. 54, No. 2, 2002, pp. 219-226, The American Society for Pharmacology and Experimental Therapeutics.

(Continued)

*Primary Examiner* — Karen Canella
(74) *Attorney, Agent, or Firm* — K&L Gates LLP; Louis C. Cullman; Dean. G. Stathakis

(57) ABSTRACT

Methods and compositions for contributing to the treatment of cancers, especially ovarian tumors, are disclosed. The methods and compositions utilize an endothelin B agonist ($ET_B$) to enhance the delivery and resulting efficacy of chemotherapeutic agent(s) (e.g., cisplatin and/or cyclophosphamide).

11 Claims, 4 Drawing Sheets

OTHER PUBLICATIONS

Davenport et al. "Classification of endothelin receptors and antagonists in clinical development", Clinical Science, copyright 2002, pp. 1S-3S, vol. 103, No. 48.

Del Bufalo et al., "Endothelin-1 acts as a survival factor in ovarian carcinoma cells", Clinical Science, copyright 2002, pp. 302S-305S, vol. 103, No. 48.

Dugan et al., "Protection against aspirin-induced human gastric mucosal injury by bosentan, a new endothelin-1 receptor antagonist", Aliment Pharmacol Ther, copyright 1999, pp. 631-635, vol. 13.

Eisenberger "Chemotherapy in Prostate Cancer", Crawford, E.D. and S. Das, Current Genitourinary Cancer Surgery, XVIII+699P, Lea and Febiger: Philadelphia, USA; London, Englakd, UK, Illus, 1990, p. 507-518.

Fabricio et al., "Essential role for endothelin ETb receptors in fever induced by LPS (E. coli) in rats", British Journal of Pharmacology, copyright 1998, pp. 542-548, vol. 125.

Filep et al. "Effects of calcium antagonists on endothelin-1-induced myocardial ischaemia and oedema in the rat", British Journal of Pharmacology (1996) 118, p. 893-900.

Jarvis et al., "ABT-627, an endothelin ETa receptor-selective antagonist, attenuates tactile allodynia in a diabetic rat model of neuropathic pain", European Journal of Pharmacology, copyright 2000, pp. 29-35, vol. 388.

Kikuchi et al. "Decreased ETb Receptor Expression in Human Metastatic Melanoma Cells", Biochemical and Biophysical Research Communications, copyright 1996, pp. 734-739, vol. 219, No. 3.

Kroodsma et al. "Endothelinen:mogelijk een nieuw farmacologisch aangrijpingspunt bij hart-en vaatziekten, nierziekten en oncologische aandoeningen", Nederlands Tijdschrift Voor Geneeskunde, copyright 1997, Sep. 20, pp. 1806-1810, vol. 141, No. 38.

Lahav et al. "An endothelin receptor B antagonist inhibits growth and induces cell death in human melanoma cells in vitro and in vivo", Proceedings of the National Academy of Sciences of USA, copyright Sep. 1999 pp. 11496-11500, vol. 96.

Matsumaru et al., "Bosentan, a novel synthetic mixed-type endothelin receptor antagonist, attenuates acute gastric mucosal lesions induced by indomethacin and HCl in the rat: Role of endogenous endothelin-1", Journal of Gastroenterology, copyright 1997 pp. 164-170 vol. 32.

McQueen et al. "Endothelin-1 activates ETA receptors to cause reflex scratching in BALB/c mice." British Journal of Pharmacology, 2007, 151, 278-284.

Murata et al. British Jounal of Pharmacology, Apr. 2011, vol. 132, pp. 1365-1373.

Rai et al. "Evidence for the involvement of ETb receptors in ET-1 induced changes in blood flow to the rat breast tumor", Cancer Chemother Pharmacol, copyright Nov. 8, 2002, pp. 21-28, vol. 51.

Rai et al., "ETb receptor agonist, IRL 1620, does not affect paclitaxel plasma pharmacokinetics in breast tumor bearing rats", Journal of Pharmacy and Pharmacology, copyright 2005, pp. 869-879, vol. 57, No. 76.

Rajeshkumar et al., "IRL-1620, a tumor selective vasodilator, augments the uptake and efficacy of chemotherapeutic agents in prostate tumor rats", Prostate, vol. 67, No. 7, 2007, p. 701-713.

Rajeshkumar et al., "ETB receptor agonist, IARL-1620, enhances the efficacy of cyclophosphamide and cisplatin in ovarian tumor bearing mice", Proceedings of the American Association of Cancer Research Annual Meeting, vol. 48, 2007, p. 961.

Rajeshkumar et al., "ET-1(8-21) Increases Blood Perfusion and Enhances Paclitaxel Delivery to the Tumor", Proceeding of the Annual meeting of the American Association for Cancer Research, New York, NY, US, copyright 2005, p. 1349, vol. 96.

Rajeshkumar et al., "Endothelin B receptor against, IRL 1620, enhances the anti-tumor efficacy of paclitaxel in breast tumor rats", Breast Cancer Research and Treatment, copyright 2005, pp. 237-247, vol. 94, No. 3.

Rowinsky et al., "Paclitaxel (Taxol)", Review Article The New England Journal of Medicine, Apr. 13, 1995, pp. 1004-1014, vol. 332.

Takai "A Potent and Specific Agonist, Suc-[Glu9, Ala11,15]—Endothelin-1(8-21), IRL 1620, for the ETB Receptor", Biochemical and Biophysical Research Communications, vol. 184, No. 2, 1992, pp. 953-959.

Takita "Effect of vasodilators in experimental solid tumor chemotherapy", Journal of Experimental and Clinical Cancer Research 1983 Italy, copyright 1999, pp. 47-48, vol. 2, No. 1 (Database Embase (online) Elsevier Science Publishers, Amsterdam).

University of Illinois At Chicago: "List of Posters Presentations in 2004 AAPS Annual Meeting (Baltimore)", www2.uic.edu/stud_orgs/prof/aaps/posters.htm, Online pp. 1-4.

Wu Recent Discovery and Development of Endothelin Receptor Antagonists, Expert Opinion on Therapeutic Patents, copyright 2000 pp. 1653-1668 vol. 10, No. 11.

Wu-Wong et al. The Journal of Pharmacology and Experimental Therapeutics, 2000, vol. 293, pp. 514-521.

Ishibashi et al. "Growth of Hepatocarcinoma and Endothelian," Annual Research Report, Foundation for Growth Science, Jul. 1996, No. 19, p. 193-204.

Nelson et al. "Endothelian-1 Production and Decreased Endothelian B Receptor Expression in Advanced Prostate Cancer," Cancer Research, Feb. 15, 1996, vol. 56, No. 4, p. 663-668.

* cited by examiner

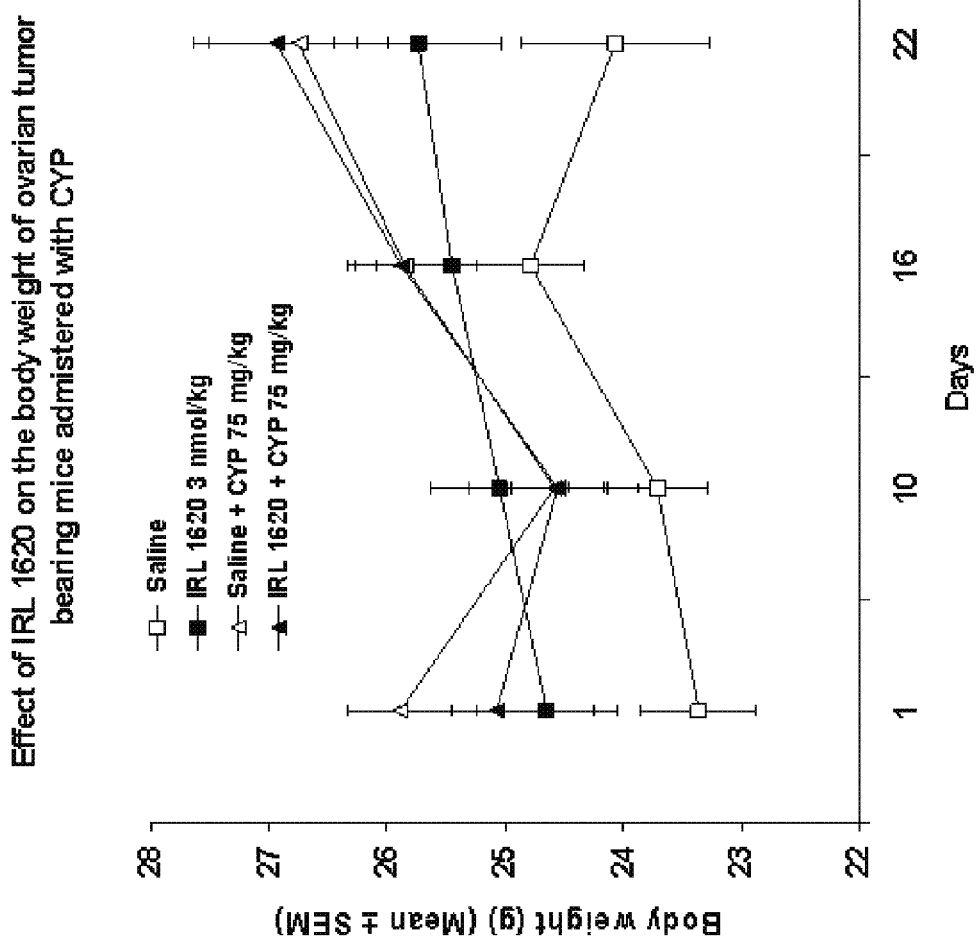

METHODS AND COMPOSITIONS FOR CONTRIBUTING TO THE TREATMENT OF CANCERS

CROSS-REFERENCE TO RELATED APPLICATIONS

This patent application is a continuation and claims the benefit of priority pursuant to 35 U.S.C. §120 to U.S. patent application Ser. No. 12/101,008, filed Apr. 10, 2008, (which claims the benefit of priority pursuant to 35 U.S.C. §119(e) to U.S. Provisional Patent Application No. 60/911,773, filed on Apr. 13, 2007), a continuation that claims priority pursuant to 35 U.S.C. §120 to U.S. patent application Ser. No. 11/461,961 filed Aug. 2, 2006, now abandoned, a continuation-in-part that claims priority pursuant to 35 U.S.C. §120 to U.S. patent application Ser. No. 11/360,236, filed Feb. 22, 2006, (which claims the benefit of priority pursuant to 35 U.S.C. §119(e) to U.S. Provisional Patent Application Nos. 60/655,656; 60/655,654; and 60/655,643, all filed on Feb. 22, 2005), a continuation-in-part that claims priority pursuant to 35 U.S.C. §120 to U.S. patent application Ser. No. 10/691,915, filed Oct. 23, 2003, now abandoned, a patent application that claims the benefit of priority pursuant to 35 U.S.C. §119(e) to U.S. Provisional Patent Application No. 60/420,960, filed Oct. 24, 2002; each of which is hereby incorporated by reference in its entirety.

FIELD OF INVENTION

The present invention relates to methods and compositions for the treatment of cancers, including solid tumors, with an endothelin agonist and at least one chemotherapeutic agent such as cyclophosphamide or cisplatin.

BACKGROUND OF INVENTION

Chemotherapy with most anticancer agents is complicated by limitations, such as low therapeutic index and host tissue toxicity, which leads to life-threatening situations and decreases the quality of life for many patients. Lack of efficacy and significant potential side effects of standard chemotherapy regimens are driving the search for novel approaches to anticancer therapy. One approach to increase the effectiveness of existing anticancer drugs for cancer treatment is to increase the uptake of drugs into the tumor thereby increasing the therapeutic tumor concentration.

Successful treatment of cancers, including solid tumors, remains an unfulfilled medical goal, despite increased understanding of the molecular biology of tumor cells and the availability of an increased number of potential therapeutic agents. For example, ovarian cancer is the fifth leading cause of cancer deaths in women, the leading cause of death from gynecological malignancy, and the second most commonly diagnosed gynecologic malignancy.

One problem in the treatment of cancers is that an effective dose of a wide variety of potential chemotherapeutic agents is restricted by these agents' non-selective, highly toxic effect on normal tissues. As a result, many patients suffer from the side effects of chemotherapy without reaping the benefits of the treatment. For example, the chemotherapeutic agents cyclophosphamide and cisplatin inhibit cellular proliferation and induces apoptosis of tumor cells. The clinical utility of cyclophosphamide and cisplatin have been hampered, however, by dose limiting toxicities. Thus, there is a necessity to develop more specific and less toxic cancer therapies.

Targeted delivery of chemotherapeutic agents to tumors could have the advantage of enhancing the benefit of chemotherapeutic agents while minimizing their systemic toxic effects. Such targeted delivery could also serve to lower the required dose of chemotherapeutic agents thus potentially reducing the unacceptable adverse effects of these agents. One possible way to achieve targeted delivery of chemotherapeutic agents is to utilize the distinctive features of tumor vasculature.

Tumors greater than a few millimeters in size require a constant nutrient supply, and, therefore, develop their own vascular bed and blood flow (Folkman, Cancer Res, 46:467 (1986)). Without constant nourishment from these developing blood vessels, the tumors become hypoxic and subsequently die. Recruitment of new vasculature from preexisting blood vessels is termed "angiogenesis."

During angiogenesis, tumor blood vessels develop substantially differently from normal vasculature, and have different properties. Single layered epithelial cells are the first hastily formed tumor blood vessels. These newly formed tumor blood vessels do not have a smooth muscle layer or innervation. Tumors also incorporate mature blood vessels that possess all their autoregulatory functions. Mattsson et al., Tumor Blood Circulation, CRC Press, Boca Raton, pg. 129 (1979); Reinhold, Tumor Blood Circulation, CRC Press, Boca Raton, pg. 115 (1979); Warren, Tumor Blood Circulation, CRC Press, Boca Raton, pg. 26 (1979).

Vascular tone (the degree to which blood vessels are dilated or constricted) is governed by a host of endogenous factors including $H^+$, $K^+$, $Ca^{2+}$, $pO_2$, $pCO_2$ and nitric oxide (NO), as well as other regulatory substances such as endothelin (ET-1). Secombe et al., Landes, Austin, pg. 40 (1994); Luscher et al., The endothelium: modulator of cardiovascular function, CRC Press, Boca Raton, pg. 61 (1990). ET-1 contributes significantly to regulating vascular tone (Yanagisawa et al., Nature, 332:411 (1988)) and investigators have shown an increase in ET1 and $ET_B$ receptor expression in solid tumors including breast carcinomas. Alanen et al., Histopathology, 36:161 (2000); Nelson et al., Cancer Res, 56:663 (1996); Kar et al., Biochem Biophys Res Commun 216:514 (1995); Pagotto et al., J Clin Invest, 96:2017 (1995); Yamashita et al., Cancer Res, 52:4046 (1992); Yamashita et al., Res Commun Chem Pathol Pharmacol, 74:363 (1991). Further, stimulation of $ET_B$ receptors causes an increase in blood supply to tumors through vasodilation of tumor blood vessels. The present disclosure takes advantage of this fact by using $ET_B$ receptor agonists to selectively increase blood flow to tumors to enhance the targeted delivery of chemotherapeutic agents

SUMMARY OF INVENTION

The present disclosure is related to selectively-increasing the uptake of anticancer agents such as cyclophosphamide and cisplatin, into tumors such as ovarian tumors by administering an $ET_B$ agonist with at least one anti-cancer agent. A treatment regimen in accordance with the present invention reduces tumor volume, such as ovarian tumor volume, in animals.

The methods of the present invention contribute to the treatment of cancer. The methods include administering to an animal in need of treatment, at least one endothelin B ($ET_B$) agonist and at least one chemotherapeutic agent. The cancers treatable in accordance with the present invention include, but are not limited to, solid tumors like ovarian tumors, colon tumors, Kaposi's sarcoma, breast tumors, melanomas, prostate tumors, meningiomas, liver tumors, breast phyllode tumors, brain tumors, neck tumors, lung tumors, and combinations of tumors. The methods of the present invention include mechanisms whereby the $ET_B$ agonist selectively increases the blood supply to the tumor thereby increasing the delivery of chemotherapeutic agent(s) to the tumor. The $ET_B$ agonist and the chemotherapeutic agents may be administered substantially simultaneously (e.g. as a single composition) or sequentially (e.g. the chemotherapeutic agent is administered prior to the $ET_B$ agonist or vice versa).

The present invention is also directed to compositions having at least one chemotherapeutic agent, at least one $ET_B$ agonist, and, optionally, at least one pharmaceutically acceptable excipient. The $ET_B$ agonist(s) and chemotherapeutic agent(s) may be part of the same composition, are provided as separate compositions, or both.

$ET_B$ agonists suitable for use in either the methods or the compositions of the present invention include, but are not limited to, ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$] ET-1, and combinations. IRL-1620 is a preferred $ET_B$ agonist.

Chemotherapeutic agents suitable for use in either the methods or the compositions of the present invention include, but are not limited to, adriamycin, camptothecin, carboplatin, cisplatin, cyclophosphamide, daunorubicin, doxorubicin, alpha interferon, beta interferon, gamma interferon, interleukin 2, irinotecan, docetaxel, paclitaxel, topotecan, 5-fluorouracil, and combinations. Cisplatin, cyclophosphamide, and their combination are preferred chemotherapeutic agents.

DETAILED DESCRIPTION OF THE INVENTION

Figure 1:
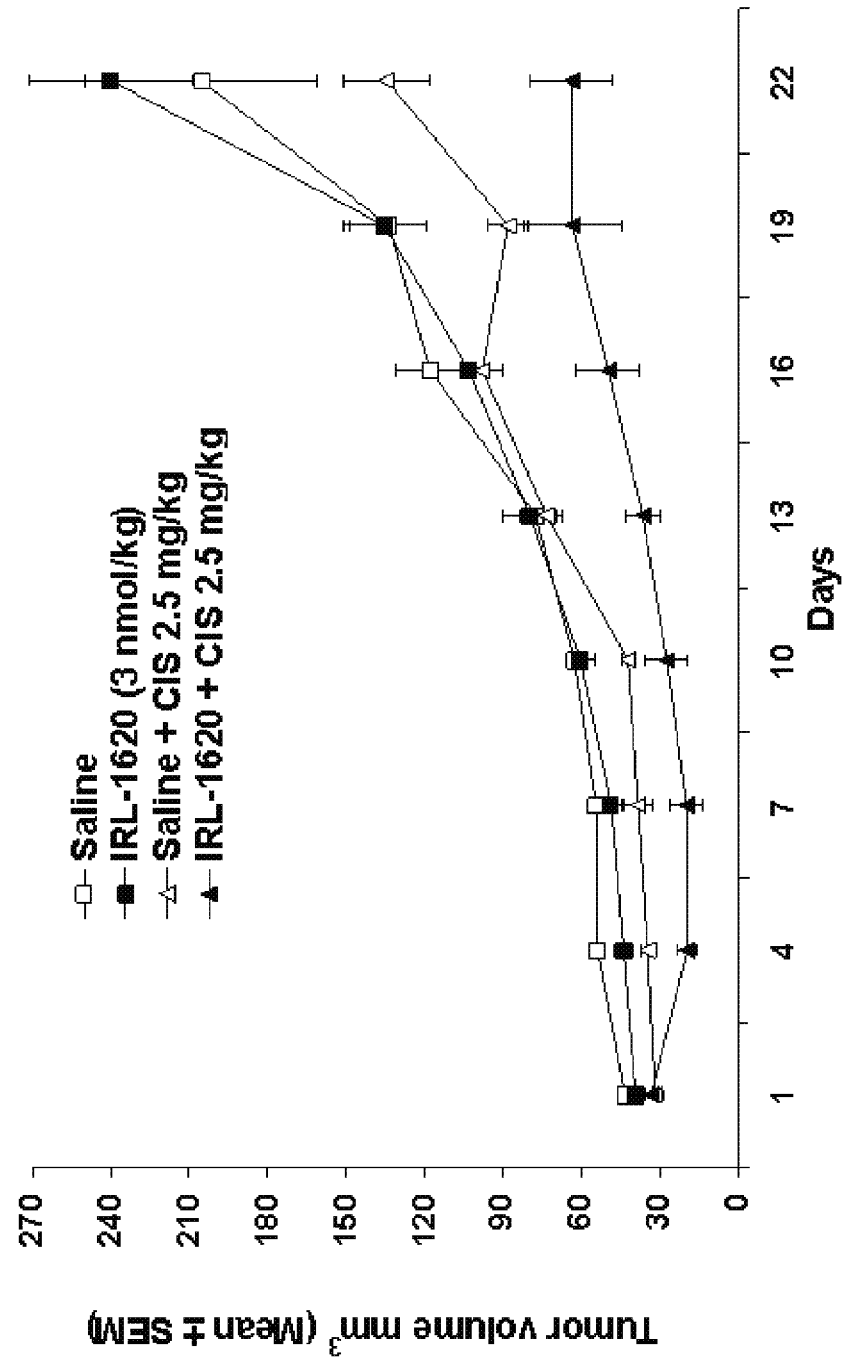
FIG. 1 depicts the tumor volume of ovarian tumor mice (N=6) separately given saline, IRL-1620 (3 nmol/kg), saline+cisplatin (2.5 mg/kg), or IRL-1620 (3 nmol/kg)+cisplatin (2.5 mg/kg) once every three days for a total of 4 doses.

The methods of the present invention contribute to the treatment of cancer. In one embodiment, the present disclosure relates to a method of contributing to the treatment of cancer comprising administering an endothelin B ($ET_B$) agonist and at least one chemotherapeutic agent.

As used herein, the terms "treat", "treatment" and "contributing to the treatment of" shall mean preventing, retarding the progression or growth of, shrinking, or eliminating a cancer including a solid tumor. As such, these terms include both medical therapeutic and/or prophylactic administration, as appropriate.

Most chemotherapeutic agents have cytotoxic properties that are targeted to destroy cancer cells, but in the process inflict considerable damage to the body's normal physiological systems. It would be of great advantage, therefore, to selectively deliver chemotherapeutic agents to solid tumors thus helping to avoid these negative effects of cancer treatment.

The angioarchitecture of tumor blood vessels is different from that of normal blood vessels. Carmeliet & Jain, Nature, 407:249 (2000). Therefore, the vascular reactivity of tumors differs from that of normal tissue. For example, the administration of nitric oxide donors, nicotinamide and bradykinin agonists modulate blood flow to tumors. Jordan et al., Int J Radiat Oncol Biol Phys, 48:565 (2000); Fukumura et al., Am J Pathol, 150:713 (1997); Hirst et al., Br J Radiol, 67: 795 (1994).

Endothelin is a vasoactive substance that modulates blood flow and is present in large concentrations in breast carcinoma tissues compared to normal breast tissue (specifically, endothelin can be present in an amount of about 12 pg/mg in breast carcinoma tissues as compared to about 0.12 pg/mg in normal breast tissue). Kojima et al., Surg Oncol, 4(6):309 (1995); Kurbel et al., Med Hypotheses, 52(4):329 (1999); Patel et al., Mol Cell Endocrinol, 126(2):143 (1997); Yamashita et al., Cancer Res, 52(14):4046 (1992); Yamashita et al., Res Commun Chem Pathol Pharmacol, 74(3):363 (1991). Endothelins are a family of cyclic peptides with 21 amino acids, comprising three isoforms in mammals, ET-1, ET-2 and ET-3. Inoue et al., Proc Natl Acad Sci USA 86:2863 (1989); Yanagisawa et al., Nature, 332:411 (1988). Endothelins exert their effects by binding to two distinct cell surface receptors, $ET_A$ and $ET_B$. The $ET_B$ receptor binds the three peptide isotypes with equal affinity. In contrast, the $ET_A$ receptor binds ET-1 with higher affinity than the other isoforms. Both receptors belong to the G protein-coupled receptor system and mediate biological responses from a variety of stimuli, including growth factors, vasoactive polypeptides, neurotransmitters and hormones. Masaki, J Cardiovasc Pharmacol, 35:S3 (2000); Gulati, Preface. Adv Drug Deliv Rev, 40:129 (2000); Gulati et al., Am J Physiol, 273:H827 (1997); Levin, N Engl J Med, 333:356 (1995). $ET_B$ receptors, a focus of the present invention, are present on both endothelial cells (ECs) and vascular smooth muscle cells (VSMCs) and are increased in breast cancer tissue (including in invasive as well as in ductal and lobular breast carcinoma tissue in humans) when compared to normal breast tissue. Wulfing et al., Oncol Rep, 11:791 (2004); Wulfing et al., Clin Cancer Res, 9:4125 (2003); Alanen et al., Histopathology, 36(2):161 (2000). Endothelin acts on $ET_B$ receptors to produce vascular dilation and increase blood flow to breast tumor tissue. $ET_B$ receptors predominating on ECs, produce vasodilatation via the release of factors such as prostacyclin and nitric oxide. de Nucci et al., Proc Natl Acad Sci USA, 85:9797 (1988). Because ET-1 produces an increase in blood flow to tumors by stimulating $ET_B$ receptors, an $ET_B$ receptor agonist can be used to selectively increase blood supply to tumors, thus increasing the targeted delivery and resulting efficacy of chemotherapeutic agents.

$ET_B$ receptors have been shown in, for example and without limitation, ovarian cancers, myofibroblasts, Kaposi's sarcoma tumor and intratumoral vessels, breast cancers and melanomas. Bagnato et al., Am J Pathol, 158:841 (2001); Alanen et al., Histopathology, 36(2):161 (2000); Bagnato et al., Cancer Res, 59:720 (1999); Kikuchi et al., Biochem Biophys Res Comm, 219:734 (1996). Therefore, administration of an $ET_B$ receptor agonist in combination with a chemotherapeutic agent can be used to contribute to the treatment of solid tumors, including, without limitation, ovarian cancer, colon carcinoma, Kaposi's sarcoma, breast cancer, and melanomas.

$ET_B$ agonists useful in accordance with the present invention include, without limitation, ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and combinations thereof. [Ala$^{1,3,11,15}$]ET-1 is a linear analog of ET-1 in which the disulfide bridges have been removed by substitution of Ala for Cys residues. Saeki et al., Biochem Biophys Res Commun, 179:286 (1991). BQ3020 and IRL1620 are truncated linear synthetic analogs of ET-1 and are the most widely used selective synthetic agonists. IRL-1620 is a linear ET-analog whose structure is based on the carboxy terminal end of ET-1 and has 120,000 fold selectivity for the $ET_B$ receptors. Okada & Nishikibe, Cardiovasc Drug Rev, 20:53 (2002); Douglas et al., Br J Pharmacol, 114:1529 (1995). IRL-1620 is a highly selective and potent $ET_B$ agonist, with evidence being reported of its selectivity for the $ET_{B1}$ receptor subtype in preference over the $ET_{B2}$ subtype. Brooks et al., J Cardiovasc Pharmacol, 26 Suppl 3:S322 (1995).

Chemotherapeutic agents useful in accordance with the present invention include, for example and without limitation, alkylating agents, antimetabolites, hormones and antagonists thereof, radioisotopes, antibodies, as well as natural products, and combinations thereof. For example, an $ET_B$ agonist can be administered with antibiotics, such as doxorubicin and other anthracycline analogs, nitrogen mustards, such as, without limitation, cyclophosphamide, pyrimidine analogs such as, without limitation, 5-fluorouracil, cisplatin, hydroxyurea, and its natural and synthetic derivatives, and the like. As another example, in the case of mixed tumors, such as adenocarcinoma of the breast, where the tumors include gonadotropin-dependent and gonadotropin-independent cells, the $ET_B$ agonist can be administered in conjunction with, without limitation, leuprolide or goserelin (synthetic peptide analogs of LH-RH). Additional non-limiting examples of chemotherapeutic agents that can be used with the present invention include cyclophosphamide, cisplatin, adriamycin, camptothecin, carboplatin, daunorubicin, doxorubicin, interferon (alpha, beta, and/or gamma), interleukin 2, irinotecan, docetaxel, paclitaxel, topotecan, and therapeutically effective analogs and derivatives of the same.

It is theorized, but not relied upon herein, that endothelin agonists stimulate $ET_B$ receptors to dilate tumor blood vessels, thereby increasing blood flow and the resultant delivery of chemotherapeutic agents to the tumor. The increased blood perfusion of tumors caused by endothelin agonists also increases oxygenation of the tissue. Improved oxygenation can enhance the therapeutic action of chemotherapeutic agents. Endothelin also can have mitogenic properties. The mitogenic actions of endothelin can help increase the action of chemotherapeutic agents, when administered together. The mitogenic action of an endothelin agonist can increase the action of chemotherapeutic agents by improving their incorporation into dividing cells, thus increasing their efficacy.

Chemotherapy is frequently indicated as an adjuvant to surgery in the treatment of a cancer. The goal of chemotherapy in the adjuvant setting is to reduce the risk of recurrence and enhance disease-free survival when the primary tumor has been controlled. Chemotherapy is utilized as a treatment adjuvant for a cancer, frequently when the disease is metastatic. An $ET_B$ agonist, therefore, is particularly useful before or following surgery in the treatment of a solid tumor in combination with chemotherapy.

In another embodiment of the present method, the cancer is a solid tumor. In another embodiment, the solid tumor is selected from the group consisting of an ovarian tumor, a colon tumor, Kaposi's sarcoma, a breast tumor, a melanoma, a prostate tumor, a meningioma, a liver tumor, a breast phyllode tumor, brain tumor, neck tumor, lung tumor, and combinations thereof. In another embodiment, the solid tumor is ovarian tumor.

In another embodiment, the $ET_B$ agonist is selected from the group consisting of ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and combinations thereof. In another embodiment, the $ET_B$ agonist is IRL-1620.

In another embodiment, the chemotherapeutic agent is selected from the group consisting of adriamycin, camptothecin, carboplatin, cisplatin, cyclophosphamide, daunorubicin, alpha interferon, beta interferon, gamma interferon, interleukin 2, irinotecan, docetaxel, paclitaxel, topotecan, 5-fluorouracil, and combinations thereof. In another embodiment, the chemotherapeutic agent is cisplatin, cyclophosphamide, or a combination thereof.

In another embodiment, the increase in the blood supply to the tumor increases the delivery of the chemotherapeutic agent to the solid tumor. In another embodiment, the $ET_B$ agonist and the chemotherapeutic agent are administered substantially simultaneously. In another embodiment, the $ET_B$ agonist and the chemotherapeutic agent are administered as a single composition. In another embodiment, the $ET_B$ agonist and the chemotherapeutic agent are administered sequentially. The chemotherapeutic agent may be administered prior to the $ET_B$ agonist or the $ET_B$ agonist may be administered prior the chemotherapeutic agent.

The present disclosure also relates to a composition comprising a chemotherapeutic agent, and $ET_B$ agonist, and an optional excipient. The $ET_B$ agonist and the chemotherapeutic agent are part of the same composition, are provided as separate compositions, or both. The $ET_B$ agonist may be selected from the group consisting of ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and combinations thereof. The $ET_B$ agonist may be IRL-1620. The chemotherapeutic agent maybe selected from the group consisting of adriamycin, camptothecin, carboplatin, cisplatin, cyclophosphamide, daunorubicin, doxorubicin, alpha interferon, beta interferon, gamma interferon, interleukin 2, irinotecan, docetaxel, paclitaxel, topotecan, 5-fluorouracil, and combinations thereof.

In another embodiment, the chemotherapeutic agent is cisplatin, cyclophosphamide, or a combination thereof and the $ET_B$ agonist is IRL-1620.

EXAMPLE

It surprisingly has been discovered that the administration of IRL-1620 and at least one anti-cancer agent selectively-increases the uptake of anticancer agents, e.g. cyclophosphamide and cisplatin, into ovarian tumors. A treatment regimen in accordance with the present invention reduces ovarian tumor volume in animals.

A preclinical efficacy study was conducted on the human ovarian tumor model in mice. The tumor cells used were SK-OV3 cells purchased from ATCC. The mice were 4-6 week old Athymic (nu+/nu+) female mice. The IRL-1620 was intravenously-infused slowly (over 30 seconds). The IRL-1620 was obtained from American Peptides, CA. The cyclophosphamide was obtained from Cadila Pharmaceuticals, Ahmedabad (Batch No. GW-4005). The cisplatin also was obtained from Cadila Pharmaceuticals, Ahmedabad (Batch No. KL-5005).

A solid tumor was induced in each animal using 3 million viable SK-OV3 cells suspended in 200 µl of PBS per animal. After 10 days, when established tumors of 100 mm$^3$ in diameter were detectable, the mice randomly were divided into six groups of 6 animals per group with each group receiving different treatments. The treatment regimens were administered via the tail vein every third day for a total of 4 doses. The groups were treated as follows: (1) tumor bearing mice received saline (N=6); (2) tumor bearing mice received IRL-1620 (3 nmol/kg) (N=6); (3) tumor bearing mice received vehicle (saline)+cyclophosphamide (75 mg/kg) (N=6); (4) tumor bearing mice received IRL-1620 (3 nmol/kg)+cyclophosphamide (75 mg/kg) (N=6); (5) tumor bearing mice received saline+cisplatin (2.5 mg/kg) (N=6); and, (6) tumor bearing mice received IRL-1620 (3 nmol/kg)+cisplatin (2.5 mg/kg) (N=6).

The effect of these treatments on the tumor size was measured using a digital caliper for a total of 12 days after drug administration. The mice were monitored and weighed on every third day. The administered doses were half of the maximum tolerated dose of cyclophosphamide and cisplatin for the human ovarian xenograft model in nude mice reported in published literature (*British Journal of Cancer* (2000) 83, 921-927). The animals were euthanized with pentobarbital 150-200 mg/kg for each mouse. Progression, stasis, partial regression or complete regression of tumor growth were measured by tumor load measurements with calipers and was calculated using the following formula: (3.14/6)×larger diameter×smaller diameter.

The results of the study are shown in the figures. FIG. 1 depicts tumor volume of ovarian tumor bearing mice given IRL-1620 (3 nmol/kg) and cisplatin (2.5 mg/kg). Six ovarian tumor bearing mice (N=6) were given saline, IRL-1620 (3 nmol/kg), saline+cisplatin (2.5 mg/kg), or IRL-1620 (3 nmol/kg)+cisplatin (2.5 mg/kg). The dosing schedule was once every three days for a total of 4 doses. Body weight and tumor volumes were measured on every third day through the 22nd day. IRL-1620/cisplatin treated mice showed more reduction in tumor volume compared to saline/cisplatin treated mice.

Figure 2:
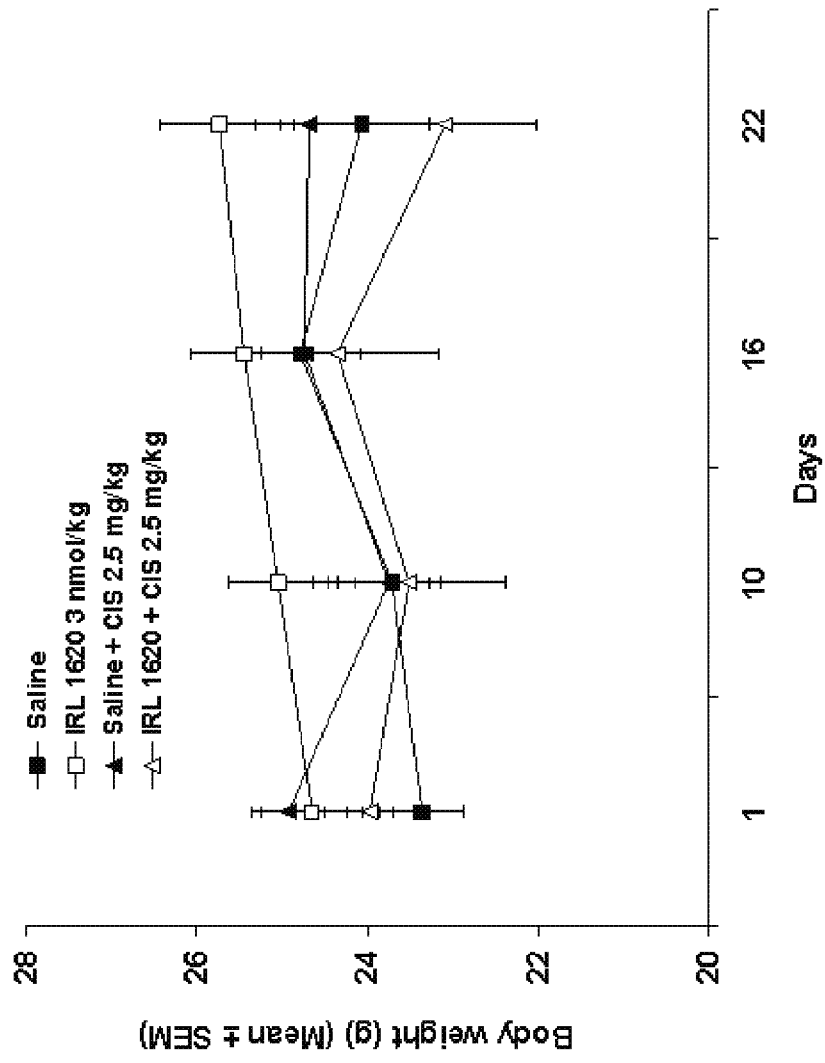
FIG. 2 depicts the body weight of ovarian tumor mice (N=6) separately given saline, IRL-1620 (3 nmol/kg), saline+cisplatin (2.5 mg/kg), or IRL-1620 (3 nmol/kg)+cisplatin (2.5 mg/kg) once every three days for a total of 4 doses.

FIG. 2 depicts body weight of ovarian tumor bearing mice given IRL-1620 (3 nmol/kg) and cisplatin (2.5 mg/kg). Six ovarian tumor bearing mice (N=6) were given saline, IRL-1620 (3 nmol/kg), saline+cisplatin (2.5 mg/kg), or IRL-1620 (3 nmol/kg)+cisplatin (2.5 mg/kg). The dosing schedule was once every three days for a total of 4 doses. Body weight and tumor volumes were measured on every third day through the 22nd day. The body weight in all groups was similar.

Figure 3:
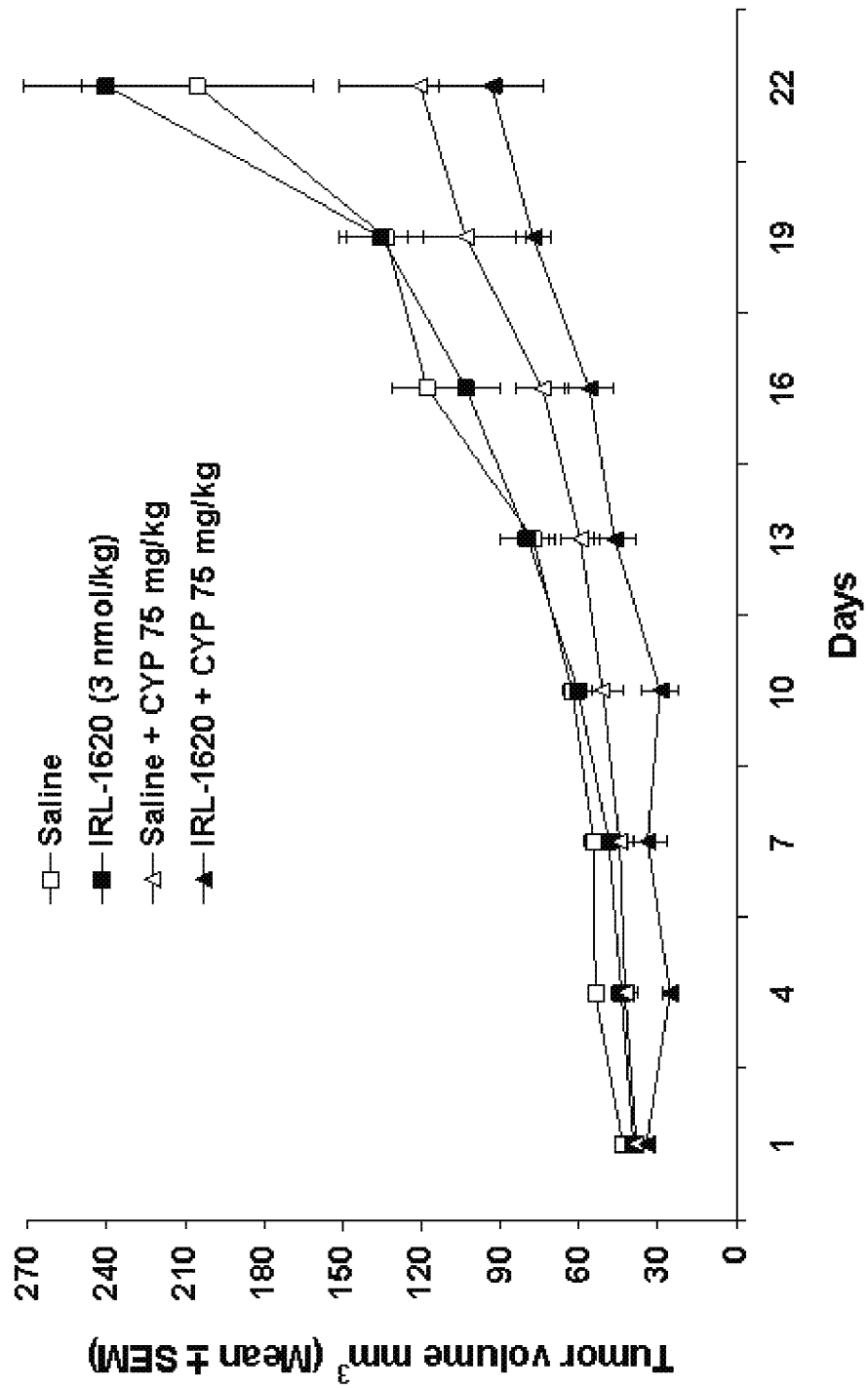
FIG. 3 depicts the tumor volume of ovarian tumor mice (N=6) separately given saline, IRL-1620 (3 nmol/kg), saline+cyclophosphamide (75 mg/kg), or IRL-1620 (3 nmol/kg)+cyclophosphamide (75 mg/kg) once every three days for a total of 4 doses; and, FIG. 4 depicts the body weight of ovarian tumor mice (N=6) separately given saline, IRL-1620 (3 nmol/kg), saline+cyclophosphamide (75 mg/kg), or IRL-1620 (3 nmol/kg)+cyclophosphamide (75 mg/kg) once every three days for a total of 4 doses.

FIG. 3 depicts tumor volume of ovarian tumor bearing mice given IRL-1620 (3 nmol/kg) and cyclophosphamide (75 mg/kg). Six ovarian tumor bearing mice (N=6) were given saline, IRL-1620 (3 nmol/kg), saline+cyclophosphamide (75 mg/kg), or IRL-1620 (3 nmol/kg)+cyclophosphamide (75 mg/kg). The dosing schedule was once every three days for a total of 4 doses. Body weight and tumor volumes were measured on every third day through the 22nd day. IRL-1620/cyclophosphamide treated mice showed more reduction in tumor volume compared to saline/cyclophosphamide treated mice.

FIG. 4 depicts body weight of ovarian tumor bearing mice given IRL-1620 (3 nmol/kg) and cyclophosphamide (75 mg/kg). Six ovarian tumor bearing mice (N=6) were given saline, IRL-1620 (3 nmol/kg), saline+cyclophosphamide (75 mg/kg), IRL-1620 (3 nmol/kg)+cyclophosphamide (75 mg/kg). Dosing schedule was once every three days for a total of 4 doses. Body weight and tumor volumes were measured on every third day through the 22nd day. The body weight in all the groups was similar.

Based on these results, it is apparent that the administration of IRL-1620 alone with, inter alia, cyclophosphamide or cisplatin contributes to the treatment of ovarian cancer tumors by reducing tumor size. There was a significant increase in the tumor volume in saline only treated ovarian tumor bearing mice. In this study, IRL-1620 alone did not significantly affect tumor volume when compared to controls. Animals treated with saline/cisplatin showed a significant reduction in tumor volume. However, IRL-1620/cisplatin treated mice showed a greater reduction in tumor volume than saline/cisplatin treated mice. Animals treated with saline/cyclophosphamide showed a significant reduction in tumor volume. However, IRL-1620/cyclophosphamide treated mice showed a greater reduction in tumor volume than saline/cyclophosphamide treated mice.

Pharmaceutical compositions containing the described active ingredients are suitable for administration to humans or other mammals. Typically, the pharmaceutical compositions are sterile, and contain no toxic, carcinogenic, or mutagenic compounds that would cause an adverse reaction when administered. Administration of the pharmaceutical composition can be performed before, during, or after the onset of solid tumor growth.

A method of the present invention can be accomplished using active ingredients as described above, or as a physiologically acceptable salt, derivative, prodrug, or solvate thereof. The active ingredients can be administered as the neat compound, or as a pharmaceutical composition containing either or both entities.

As used herein, the term "prodrug" shall mean compounds that transform rapidly in vivo to a compound useful in the invention, for example, by hydrolysis. A thorough discussion of prodrugs is provided in Higuchi et al., Prodrugs as Novel Delivery Systems, Vol. 14, of the A.C.S.D. Symposium Series, and in Roche (ed.), Bioreversible Carriers in Drug Design, American Pharmaceutical Association and Pergamon Press, 1987.

The pharmaceutical compositions include those wherein the active ingredients are administered in an effective amount to achieve their intended purpose. More specifically, a "therapeutically effective amount" means an amount effective to prevent development of, to eliminate, to retard the progression of, or to reduce the size of a solid tumor. Determination of a therapeutically effective amount is well within the capability of those skilled in the art, especially in light of the detailed disclosure provided herein.

A "therapeutically effective dose" refers to that amount of the active ingredients that results in achieving the desired effect. Toxicity and therapeutic efficacy of such active ingredients can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the active ingredients preferably lies within a range of circulating concentrations that include the $ED_{50}$ with little or no toxicity. The dosage can vary within this range depending upon the dosage form employed, and the route of administration utilized.

The exact formulation and dosage is determined by an individual physician in view of the patient's condition. Dosage amount and interval can be adjusted individually to provide levels of the active ingredients that are sufficient to maintain therapeutic or prophylactic effects.

The amount of pharmaceutical composition administered can be dependent on the subject being treated, on the subject's weight, the severity of the affliction, the manner of administration, and the judgment of the prescribing physician.

The active ingredients can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active ingredients into preparations which can be used pharmaceutically.

As used herein, excipients may be pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

When a therapeutically effective amount of the active ingredients is administered, the composition can be in the form of a pyrogen-free, parenterally acceptable aqueous solution. The preparation of such parenterally acceptable solutions, having due regard to pH, isotonicity, stability, and the like, is within the skill in the art. A preferred composition for intravenous injection typically will contain an isotonic vehicle although this characteristic is not required.

For veterinary use, the active ingredients are administered as a suitably acceptable formulation in accordance with normal veterinary practice. The veterinarian can readily determine the dosing regimen that is most appropriate for a particular animal.

Various adaptations and modifications of the embodiments can be made and used without departing from the scope and spirit of the present invention which can be practiced other than as specifically described herein. The above description is intended to be illustrative, and not restrictive. The scope of the present invention is to be determined only by the claims.

The terms and expressions which have been employed herein are used as terms of description and not of limitation, and there is no intention in the use of such terms and expressions of excluding equivalents of the features shown and described, or portions thereof, it being recognized that various modifications are possible within the scope of the present invention claimed. Moreover, any one or more features of any embodiment of the present invention can be combined with any one or more other features of any other embodiment of the present invention, without departing from the scope of the present invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. An article of manufacture comprising: (a) a packaged composition comprising an IRL-1620, (b) a packaged composition comprising a chemotherapeutic agent; (c) an insert providing instructions for the administration of (a) and (b) for the treatment of an ovarian tumor in a mammal; and (d) a container for (a), (b), and (c).

2. The article of manufacture according to claim 1, wherein said chemotherapeutic agent is selected from the group consisting of adriamycin, camptothecin, carboplatin, cisplatin, daunorubicin, doxorubicin, alpha interferon, beta interferon, gamma interferon, interleukin 2, irinotecan, docetaxel, paclitaxel, topotecan, and mixtures thereof.

3. The article of manufacture according to claim 1, wherein said chemotherapeutic agent is paclitaxel.

4. The article of manufacture according to claim 1, wherein when said instructions are followed, said IRL-1620 selectively increases blood supply to said ovarian tumor thus increasing the delivery of said chemotherapeutic agent to said ovarian tumor.

5. The article of manufacture according to claim 1, wherein the pharmacokinetics of said chemotherapeutic agent are not affected by said IRL-1620.

6. The article of manufacture according to claim 1, wherein said IRL-1620 enhances the efficacy of said chemotherapeutic agent.

7. An article of manufacture comprising: (a) a packaged composition comprising an IRL-1620; (b) a packaged composition comprising a chemotherapeutic agent; (c) an insert providing instructions for a simultaneous or sequential administration of (a) and (b) to treat an ovarian tumor in a mammal; and (d) a container for (a), (b), and (c).

8. The article of manufacture according to claim 7, wherein said chemotherapeutic agent is selected from the group consisting of adriamycin, camptothecin, carboplatin, cisplatin, daunorubicin, doxorubicin, alpha interferon, beta interferon, gamma interferon, interleukin 2, irinotecan, docetaxel, paclitaxel, topotecan, and mixtures thereof.

9. The article of manufacture according to claim 7, wherein said chemotherapeutic agent is paclitaxel.

10. The article of manufacture according to claim 7, wherein said insert provides instructions that the IRL-1620 is administered prior to the chemotherapeutic agent.

11. An article of manufacture comprising: (a) a packaged composition comprising an IRL-1620; (b) a packaged composition comprising a paclitaxel; (c) an insert providing instructions for a simultaneous or sequential administration of (a) and (b) to treat an ovarian tumor in a mammal; and (d) a container for (a), (b), and (c).

* * * * *